United States Patent
Speiser

Patent Number: 6,004,317
Date of Patent: Dec. 21, 1999

[54] ELECTROSURGICAL INSTRUMENT

[75] Inventor: Eric N. Speiser, St. Petersburg, Fla.

[73] Assignee: Aaron Medical Industries, Inc., St. Petersburg, Fla.

[21] Appl. No.: 08/975,462

[22] Filed: Nov. 21, 1997

Related U.S. Application Data

[62] Division of application No. 08/554,712, Nov. 7, 1995, Pat. No. 5,693,050.

[51] Int. Cl.$^6$ .................................................. A61B 17/32
[52] U.S. Cl. .................................. 606/41; 606/45; 606/50
[58] Field of Search ............................................ 606/41–52

[56] References Cited

U.S. PATENT DOCUMENTS

| | | |
|---|---|---|
| 4,314,559 | 2/1982 | Allen . |
| 4,622,966 | 11/1986 | Beard . |
| 4,785,807 | 11/1988 | Blanch . |
| 4,848,353 | 7/1989 | Engel . |
| 4,876,110 | 10/1989 | Blanch . |
| 4,924,882 | 5/1990 | Donovan . |
| 5,100,402 | 3/1992 | Fan . |
| 5,197,962 | 3/1993 | Sansom . |
| 5,380,321 | 1/1995 | Morris ........................................ 606/45 |
| 5,382,247 | 1/1995 | Cimino . |
| 5,697,926 | 12/1997 | Weaver ....................................... 606/41 |

*Primary Examiner*—David M. Shay
*Attorney, Agent, or Firm*—Arthur W. Fisher, III

[57] ABSTRACT

An electrosurgical instrument comprising a work implement having a medically acceptable working edge with a plurality of layers of different compositions including an inner primer layer with an electrically conductive polymer with a coating thickness of about 0.3 mil, an intermediate layer having a coating thickness of about 0.1 mil and an outer protective layer having a low coefficient of friction with a thickness of about 0.3 mil to reduce the adhesion of charred tissue during surgical procedures involving cauterization or cutting of tissue utilizing high frequency electrical energy as the source of power.

15 Claims, 1 Drawing Sheet

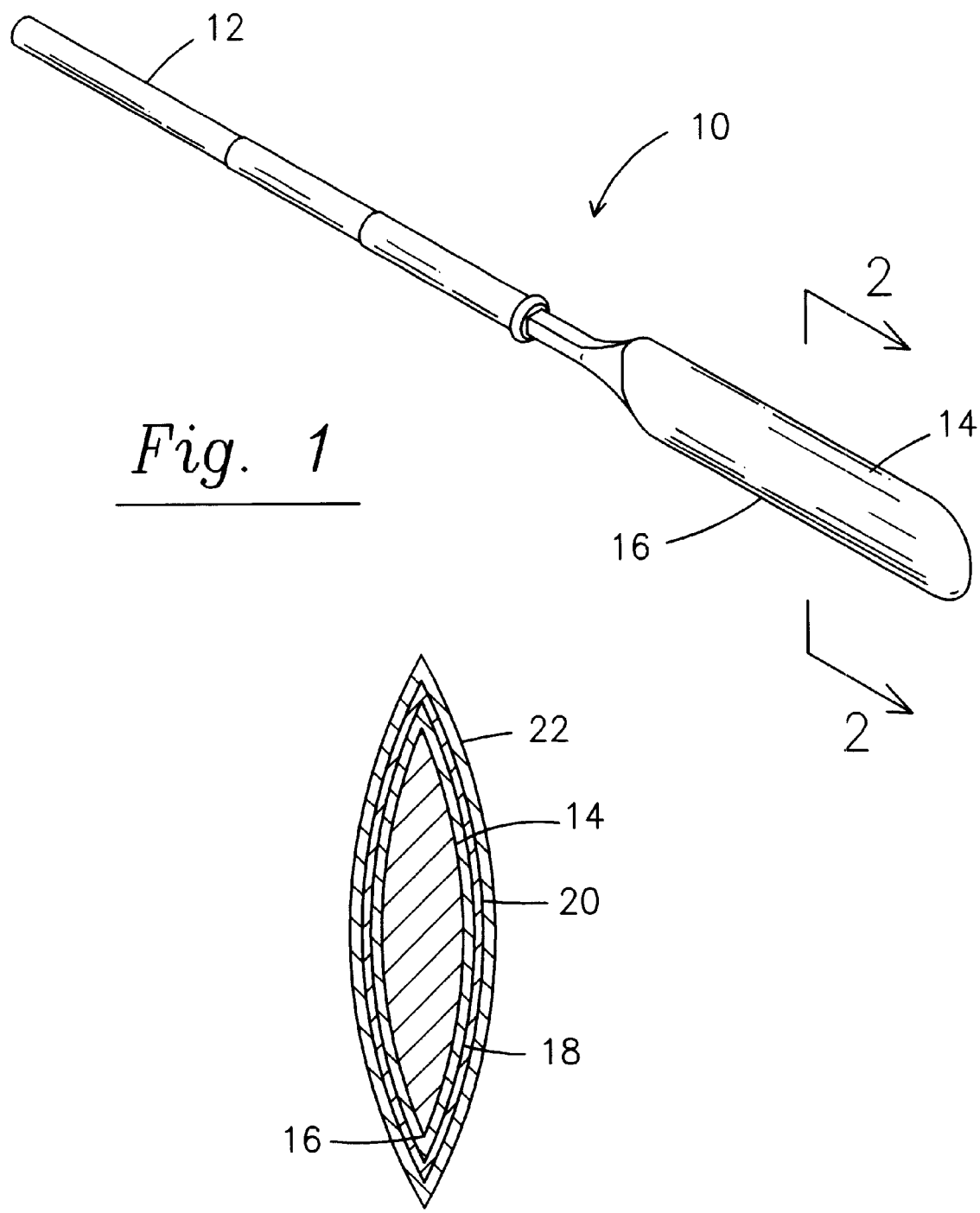

ELECTROSURGICAL INSTRUMENT

CROSS REFERENCE

This is a divisional application for allowed application Ser. No. 554,712, filed Nov. 7, 1995, now U.S. Pat. No. 5,693,050.

BACKGROUND OF THE INVENTION

1. Field of the Invention

An electrosurgical instrument comprising a work implement coated with a plurality of layers of different compositions to reduce sticking and tissue charring when in use.

2. Description of the Prior Art

Electrically powered instruments such as coagulation forceps, suction cauteries, electrode cautery tips and blade electrodes are well known. Such medical instruments are used in procedures that involve cutting and other contact with flesh or tissue. For example, surgical blade electrodes are utilized to reduce bleeding by cauterizing the exposed tissue. Typically, a blade electrode is affixed to a handpiece activated for passing electrical energy into the blade electrode to transmit radio-frequency electrical energy to the flesh or tissue to cauterize the site. Other electrosurgical devices are similarly designed. Unfortunately, sticking or charring of the cauterized tissue and blood on the medical implement can occur.

Various coatings covering a portion or the entire working surface have been used on the cauterizing instruments to render the surfaces less adherent. Coating the entire surface greatly reduces the problem of sticking and charring but results in dull cutting edges. On the other hand, coating only a portion of the working surface results in charring and sticking on the bare portion.

Much of the prior art has reduced the adherence of tissue to electrosurgical instruments. However, it has been necessary to coat essentially the entire surface that comes in contact with the flesh or tissue and the like or not exceed a low level of metallic islands in order to achieve an acceptable level of charring and adherence. Moreover, the addition of a coating which completely eliminates metallic contact with tissue resulted in some undesired dulling of these electrosurgical instruments which are also used for cutting.

U.S. Pat. No. 5,197,962 describes an electrosurgical instrument for causing hemostasis having a first predetermined region for contact with flesh or tissue. At least a portion of the predetermined region by a composite coating consisting essentially of a nickel-phosphorous matrix having particles of polytetrafluoroethylene distributed substantially uniformly therethrough.

U.S. Pat. No. 4,785,807 shows an electrosurgical knife including a stainless steel blade having an abraided or etched surface, a first coat of primer material is applied over the blade where the surface of the primer material is also abraided or etched. A second coat of non-stick fluorinated hydrocarbon material is applied over the coat of primer material having a total thickness of about three mils permitting conduction of radio-frequency electrical energy from the blade through the coatings to the tissue being cut.

The method of manufacturing the electrosurgical knife disclosed in U.S. Pat. No. 4,785,807 is shown in U.S. Pat. No. 4,876,110.

U.S. Pat. No. 5,100,402 teaches a laparoscopic cauterization electrode for use with an electrical power source for deep surgical operations through an opening in a body such as deep thorax, abdominal perineal, deep rectum, deep gynecological and similar deep body operations. The laparoscopic cauterization electrode comprises an electrically conductive electrode shaft for insertion through the body opening having a proximal end connected to the electric power source and a distal end having teflon-coated operative tip.

SUMMARY OF THE INVENTION

The present invention relates to an electrosurgical instrument such as an electrosurgical blade having a proximal end for insertion into a handle and a distal end portion including a working edge or surface to contact the flesh or tissue of the patient when the electrosurgical blade is in use. Although an electrosurgical blade for cutting and cauterizing is disclosed and described, the present invention is applicable to any electrosurgical instrument that comes into contact with the flesh and tissue of the patient such as the coagulation forceps, suction cautery devices and electrode cautery tips.

The distal end portion including the working edge or surface is coated with a plurality of layers of different compositions including an inner primer layer to provide an electrically conductive medium and to form a base to which an intermediate layer and an outer protective layer adhere with the necessary structural integrity and thermal stability. The intermediate layer provides the desired color to the distal end portion and contributes to the lubricious characteristics of the working edge or surface; while, outer protective layer resists oxidation and corrosiveness of chemicals including strong acids, bases and oxidizing agents, as well as resistance to nuclear radiation and ultraviolet rays. In addition, the outer protective layer has a low coefficient of friction.

When in use, the working edge or surface contacts the flesh or tissue of a patient and inhibits the adhering of the tissue to the instrument. Furthermore, the aggregate thickness of the inner primer layer, intermediate layer and outer protective layer and the electric conductive properties of the plurality of layers allows sufficient energy to be transferred from the working edge or surface to the patient to cut or cauterize the site to reduce bleeding while providing the required working implement.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 1 is a perspective view of an electrosurgical blade of the present invention.

FIG. 2 is a cross-section view of the electrosurgical blade of the present invention taken along line 2—2 of FIG. 1.

Similar reference characters refer to similar parts throughout the several views of the drawings.

Detailed Description of the Preferred Embodiment

As shown in FIG. 1, the present invention relates to an electrosurgical instrument such as an electrosurgical blade generally indicated as 10 having a proximal end portion 12 for insertion into a handle (not shown) or the like and a distal end portion 14 including a working edge or surface 16 to contact the flesh or tissue of the patient when the electrosurgical blade 10 is in use. The proximal end portion 12 is inserted into the handle (not shown) to supply electric current from a source (not shown) to the electrosurgical blade 10 or other electrosurgical instrument to cut and/or coagulate the site. Although an electrosurgical blade 10 for cutting and cauterizing is disclosed and described, the present invention is applicable to any electrosurgical instrument that comes into contact with the flesh and tissue of the patient such as the coagulation forceps, suction cautery devices and electrode cautery tips.

As best shown in FIG. 2, the distal end portion 14 including the working edge or surface 16 is coated with a plurality of layers of different compositions comprising an inner primer layer 18, an intermediate layer 20 and an outer protective layer 22.

The inner primer layer 18 comprises a first coat, DuPont Product No. 459-780, formulated to provide an electrically conductive medium and to form a base to which the intermediate layer 20 and the outer protective layer 22 adhere with necessary structural integrity and thermal stability. Experimentation has demonstrated that DuPont 459-780 is particularly suitable for the first coat. The first coat is applied to the working edge or surface 16 to a thickness of about 0.3 mil.

The intermediate layer 20 comprises a second coat, DuPont Product No. 456-186, formulated to provide the desired color to the distal end portion 14 and enhance the lubricious characteristics to the working edge or surface 16. In particular. The second coat is applied to the working edge or surface 16 to a thickness of about 0.1 mil. Experimentation has shown that Dupont is particularly suitable fir the intermediate layer.

The outer protective layer 22 comprises a third coat, DuPont Product No. 456-780, is formulated to resist oxidation and corrosiveness of chemicals including strong acids, bases and oxidizing agents, as well as resistance to nuclear radiation and ultraviolet rays. In addition, the third coat has low coefficient of friction of from about 0.05 to about 0.13. Experimentation has proven that Dupont is particularly suitable for the outer layer. The third coat is applied to the working edge or surface 16 to a thickness of about 0.3 mil or less.

The method of producing the electrosurgical instrument such as an electrosurgical blade 10 comprises the following steps in sequence:

(1) abrading the distal end portion 14 of the electrosurgical blade 10;

(2) applying the first coat of DuPont Product No. 459-780 to the distal end portion 14 of the electrosurgical blade 10 to a thickness of about 0.3 mil;

(3) drying the first coat applied to the distal end portion 14 of the electrosurgical blade 10 at approximately 300 degrees F for approximately 15 minutes;

(4) allowing the first coat of the distal end portion 14 of the electrosurgical blade 10 to cool;

(5) applying the second coat of DuPont Product No. 456-186 to the distal end portion 14 of the electrosurgical blade 10 to a thickness of about 0.1 mil;

(6) applying the third coat of DuPont Product No. 456-780 to the distal end portion 14 of the electrosurgical blade 10 to a thickness of about 0.3 mil; and, (7) sintering the distal end portion 14 of the electrosurgical blade 10 at approximately 780 degrees F for approximately 3 minutes.

When in use, the working edge or surface 16 contacts the flesh or tissue of a patient without charring or adhering to the patient. Furthermore, the aggregate thickness of the inner primer layer 18, intermediate layer 20 and outer protective layer 22 and the conductive properties of the plurality of layers allows sufficient energy to be transferred from the working edge or surface 16 to the patient to cut or cauterize the site to reduce bleeding while providing the required working implement.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An electrosurgical instrument comprising a work implement having a medically acceptable working edge formed on the distal end portion thereof with a plurality of layers of different compositions comprising an inner primer layer with an electrically conductive polymer, an intermediate layer to provide texture to the distal end portion, and an outer protective layer having a low coefficient of friction to reduce the adhesion of charred tissue during surgical procedures involving cauterization or cutting of tissue utilizing high frequency electrical energy as the source of power.

2. The electrosurgical instrument of claim 1 wherein said inner primer layer comprises a first coat formulated to provide an electrically conductive medium and to form a base to which said intermediate layer and said outer protective layer adhere with necessary structural integrity and thermal stability, said intermediate layer comprises a second coat formulated to provide texture to the distal end portion and the lubricity characteristics to the working edge and said outer protective layer comprises a third coat formulated to resist oxidation and corrosiveness of chemicals including strong acids, bases and oxidizing agents.

3. The electrosurgical instrument of claim 2 wherein the aggregate thickness of said first coat, said second coat and said third coat is about 0.7 mil.

4. The electrosurgical instrument of claim 3 wherein the thickness of said first coat is about 0.3 mil, the thickness of said second coat is about 0.1 mil and the thickness of said third coat is about 0.3 mil.

5. The electrosurgical instrument of claim 3 wherein the thickness of said first coat is about 0.3 mil.

6. The electrosurgical instrument of claim 5 wherein the thickness of said second coat is about 0.1 mil.

7. The electrosurgical instrument of claim 6 wherein the thickness of said third coat is about 0.3 mil.

8. The electrosurgical instrument of claim 5 wherein the thickness of said third coat is about 0.3 mil.

9. The electrosurgical instrument of claim 8 wherein the thickness of said second coat is about 0.1 mil.

10. The electrosurgical instrument of claim 3 wherein the thickness of said second cost is about 0.1 mil.

11. The electrosurgical instrument of claim 10 wherein the thickness of said third coat is about 0.3 mil.

12. The electrosurgical instrument of claim 11 wherein the thickness of said first coat is about 0.3 mil.

13. The electrosurgical instrument of claim 3 wherein the thickness of said third coat is about 0.3 mil.

14. The electrosurgical instrument of claim 13 wherein the thickness of said second coat is about 0.1 mil.

15. The electrosurgical instrument of claim 14 wherein the thickness of said first coat is about 0.3 mil.

* * * * *